| United States Patent [19] | [11] | 4,377,709 |
|---|---|---|
| Müller | [45] | Mar. 22, 1983 |

[54] PROCESS FOR THE MANUFACTURE OF 5-OXOALKANOIC ACIDS

[75] Inventor: Werner H. Müller, Eppstein, Fed. Rep. of Germany

[73] Assignee: Hoechst Aktiengesellschaft, Frankfurt am Main, Fed. Rep. of Germany

[21] Appl. No.: 218,027

[22] Filed: Dec. 19, 1980

[30] Foreign Application Priority Data

Dec. 22, 1979 [DE] Fed. Rep. of Germany ....... 2952044

[51] Int. Cl.³ ............................................. C07C 51/00
[52] U.S. Cl. .................................. 562/459; 260/405; 562/503; 562/508; 562/577; 562/578
[58] Field of Search .............. 562/459, 577, 578, 503, 562/508; 260/405

[56] References Cited

FOREIGN PATENT DOCUMENTS 2540972 3/1977 Fed. Rep. of Germany ...... 562/577
8482 3/1980 European Pat. Off. .
13254 7/1980 European Pat. Off. ............ 562/577

OTHER PUBLICATIONS

Casinos, J. Chem. Soc., 12, pp. 1651–1655, (1978).
Adams, "Organic Reactions," vol. 10, pp. 179–187 & 264–266, (1960).

*Primary Examiner*—Michael L. Shippen
*Attorney, Agent, or Firm*—Curtis, Morris & Safford

[57] ABSTRACT

5-Oxoalkanoic acids are prepared by addition of a ketone containing at least one hydrogen atom in the α-position with regard to the keto group, to an α,β-unsaturated acid. As catalysts secondary amines are present.

3 Claims, No Drawings

PROCESS FOR THE MANUFACTURE OF 5-OXOALKANOIC ACIDS

It is known to prepare 5-oxoalkanoic acids or esters or nitriles thereof by addition of a ketone containing at least one hydrogen atom in the α-position with regard to the keto group, to α,β-unsaturated acids, esters or nitriles when using a primary amine as the catalyst (cf., for example German Pat. No. 2,329,923; German Offenlegungsschriften No. 2,325,160 and 2,355,859 and German Pat. No. 2,348,536 and 2,540,972). A great disadvantage of this method of preparing the 5-oxoalkanoic acids is to be seen in the increased formation of ketone condensation products. When preparing 5-oxohexanoic acid from acetone and acrylic acid, up to 50% of the acetone consumed can be converted into mesityl oxide. It is true that the further formation of mesityl oxide can be suppressed by operating at an elevated mesityl oxide concentration in the reaction mixture. This method involves, however, considerable expenditure, since mesityl oxide has to be separated from the reaction product and be subsequently recycled. An elevated concentration of mesityl oxide moreover involves the danger of the formation of secondary products due to a further reaction of mesityl oxide with acetone, acrylic acid or amines.

It is, accordingly, an object of the present invention to avoid formation of ketone condensation products in the manufacture of 5-oxoalkanoic acids and to improve the selectivity of the latter with respect to the α,β-unsaturated acid consumed.

A process has now been found for the manufacture of 5-oxoalkanoic acid by addition of a ketone containing at least one hydrogen atom in the α-position with regard to the keto group, to an α,β-unsaturated acid at elevated temperature, which comprises carrying out the reaction in the presence of a secondary amine as catalyst.

Previously the manufacture of 5-oxoalkanoic acids, esters or nitriles thereof from ketones and α,β-unsaturated acids or esters or nitriles of the latter, has been carried out only with primary amines or with compounds containing a primary amino group, as the catalyst.

It was therefore very surprising that secondary amines, when used in the manufacture of 5-oxoalkanoic acid, are still somewhat more active than primary amines. Moreover the formation of by-products due to an autocondensation of the feed ketones is reduced and the selectivity of the oxoalkanoic acids, referred to α,β-unsaturated acid consumed is improved.

Suitable ketones for the reaction are those containing at least one hydrogen atom in the α-position with regard to the keto group, for example acetone, methyl ethyl ketone, diethyl ketone, methyl propyl ketone, methyl isopropyl ketone, hexanone-2, heptanone-2, octanone-2, nonanone-2, acetylacetone, acetonyl acetone, cyclopentanone, cyclohexanone, acetophenone, propiophenone and phenylacetone.

Examples of suitable α,β-unsaturated acids are acrylic acid, methacrylic acid, maleic acid, fumaric acid and itaconic acid.

As catalysts there may be used particularly secondary aliphatic and cycloaliphatic amines containing $C_1$-$C_8$ alkyl groups such as dimethylamine, methyl ethylamine, diethylamine, dipropylamine, diisopropylamine, dibutylamine, diisobutylamine, N-ethyl butylamine, di-(2-ethylhexyl)-amine, N-cyclohexyl methylamine, piperidine, pyrrolidine, morpholine and N-methylpiperazine. The quantity of catalyst used is in general in the range of from 0.03 to 0.3 mol per mol of α,β-unsaturated acid.

The molar ratio of ketone to unsaturated acid may vary within wide limits and is in general in the range of from 1:1 to 20:1, preferably of from 2:1 to 8:1.

The most suitable reaction temperature depends on the nature and on the quantity of the ketone, the α,β-unsaturated acid and the catalyst used. A temperature of from 100° to 250° C., preferably of from 150° C. to the critical temperature of the reaction partners used is generally chosen.

The pressure is generally adjusted such that it is between the vapor pressure corresponding to the reaction temperature and 300 bar, preferably of between the vapor pressure and 100 bar. The pressure increase beyond the vapor pressure of the reaction components may be achieved by the liquid pressure which establishes when the reactor used for the reaction is charged with the reaction components at room temperature at least to such a degree that the gas phase vanishes on heating of the reactor to the reaction temperature. A further appropriate method of achieving this pressure increase, especially with higher boiling ketones that contain more than 6 carbon atoms consists in introducing an inert gas such an $N_2$ or argon into the reactor under a pressure exceeding the vapor pressure of the reaction components.

Operating under elevated pressure results in particular in an increase in the space-time yield (g/l.h). The reaction may be performed in the presence or in the absence of a solvent or diluent. A polymerization inhibitor such as hydroquinone, hydroquinone monomethyl ether or phenothiazine is added suitably.

When operating in the discontinuous manner, the process of the invention may be carried out as follows: The reaction components are intermixed at room temperature and fed into a reactor such as an autoclave or a bomb tube, heated for a defined period of time to the desired reaction temperature, cooled rapidly, analyzed and worked up by way of distillation.

When operating in continuous manner, the process of the invention is suitably run as follows: A mixture consisting, for example, of acetone, acrylic acid, polymerization inhibitor and diethylamine is mixed thoroughly and subsequently pumped through a reaction tube heated to the desired reaction temperature. This tube is equipped at its outlet with an automatic level and pressure control. The desired reaction pressure is adjusted by superposition with an inert gas. The reaction mixture is distilled continuously immediately. The unreacted starting materials are recycled immediately.

The following examples illustrate the invention:

COMPARATIVE EXAMPLE (using primary amine)

A bomb tube of 30 ml volume is charged with 24 ml of the following starting mixture, sealed and immersed into an oil bath of 230° C. for 60 minutes, whereupon it is cooled and the contents are analyzed.

The abbreviations used in the examples are defined as follows:

Sel X/Y = mol of final product X per mol of consumed starting material Y (mol %),
Ac = acetone,
IPA = isopropylamine,
AA = acrylic acid,
OHA = 5-oxohexanoic acid,
HQ = hydroquinone, MO = mesityl oxide.

| Starting mixture (weight %) | Ac | AA | IPA | HQ |
|---|---|---|---|---|
| | 78.9 | 19.6 | 1.43 | 0.05 |

| Product composition (weight %) | | | | Sel | | |
|---|---|---|---|---|---|---|
| Ac | AA | OHA | MO | OHA/AA | OHA/Ac | MO/Ac |
| 62.7 | 4.9 | 19.1 | 5.2 | 72 | 53 | 38 |

EXAMPLES 1-3

These examples are carried out analogously to the comparative example, however, with the use of different secondary amines as the catalyst, as shown in the following table:

| Example | Starting mixture (weight %) | | | | Reaction product (weight %) | | | | Sel | | |
|---|---|---|---|---|---|---|---|---|---|---|---|
| | Ac | AA | catalyst | HQ | Ac | AA | OHA | MO | OHA/AA | OHA/Ac | MO/Ac |
| 1 | 78.6 | 19.5 | Pip 1.8 | 0.05 | 65.8 | 5.6 | 20.3 | 3.0 | 80 | 68 | 26 |
| 2 | 78.4 | 19.5 | Morph 2.0 | 0.05 | 66.2 | 6.8 | 19.3 | 2.5 | 84 | 71 | 24 |
| 3 | 78.7 | 19.5 | DEA 1.7 | 0.05 | 64.8 | 4.9 | 22.4 | 2.5 | 85 | 72 | 21 |

Example 1: piperdine = Pip
Example 2: morpholine = Morph
Example 3: diethylamine = DEA

EXAMPLE 4

Preparation of 3-(2-oxocyclohexyl)propanoic acid 24 ml of a mixture consisting of 20 g of cyclohexanone, 7.7 g of acrylic acid and 1.5 g of diethylamine are heated to 230° C. for 30 minutes in a bomb tube of 30 ml volume, cooled and analyzed by gas chromatography. The reaction product contains in addition to unreacted starting material 40% of 3-(2-oxocyclohexyl)propanoic acid, 11% of 3-(2-oxocyclohexyl)propanoic acid diethylamide (boiling point 139° C. under 1.2 mbar) and 4% of cyclohexenyl cyclohexanone.

EXAMPLE 5

Preparation of 4-phenyl-5-oxohexanoic acid 75 g of a mixture consisting of 74.4% of benzyl methyl ketone, 21.6% of acrylic acid and 4.1% of diethylamine are heated to 230° C. for 30 minutes, cooled and analyzed by gas chromatography. The reaction product contains in addition to unreacted starting material 20% of 4-phenyl-5-oxohexanoic acid (boiling point 141°-143° C. at 2 mbar) and 5% of an unknown compound having a longer retention time than 4-phenyl-5-oxohexanoic acid.

What is claimed is:

1. In a process for the manufacture of 5-oxoalkanoic acid consisting essentially of reacting a ketone containing at least one hydrogen atom in the α-position with respect to the keto group with an α, β-unsaturated acid at elevated temperature, the improvement which consists essentially of conducting said reaction with the use of a secondary amine catalyst.

2. The process of claim 1 wherein said catalyst is a secondary amine selected from the group consisting of dimethylamine, methyl ethylamine, diethylamine, dipropylamine diisopropylamine, dibutylamine, diisobutylamine, N-ethyl butylamine, di-(2-ethylhexyl)-amine, N-cyclohexyl methylamine, piperdine, pyrrolidine, morpholine and N-methylpiperazine.

3. The process of claims 1 or 2 wherein said catalyst is present in a concentration of 0.03 to 0.3 moles per mole of α,β-unsaturated acid.

* * * * *